(12) United States Patent
Leng et al.

(10) Patent No.: US 9,598,356 B2
(45) Date of Patent: Mar. 21, 2017

(54) PROCESS FOR THE MANUFACTURE OF R-(+)-2-(4-(4-CYANO-2-FLUOROPHENOXY) PHENOXY)PROPIONIC ACID ESTERS

(75) Inventors: Ronald B. Leng, Midland, MI (US); Eric W. Otterbacher, Midland, MI (US); Herbert N. Praay, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 407 days.

(21) Appl. No.: 13/034,054

(22) Filed: Feb. 24, 2011

(65) Prior Publication Data

US 2011/0152560 A1    Jun. 23, 2011

Related U.S. Application Data

(62) Division of application No. 12/251,005, filed on Oct. 14, 2008, now Pat. No. 8,071,804.

(60) Provisional application No. 61/000,256, filed on Oct. 24, 2007.

(51) Int. Cl.
*C07C 69/76* (2006.01)
*C07C 253/30* (2006.01)

(52) U.S. Cl.
CPC .................. *C07C 253/30* (2013.01)

(58) Field of Classification Search
USPC ........................................... 560/55
See application file for complete search history.

(56) References Cited

U.S. PATENT DOCUMENTS 4,894,085 A    1/1990   Pews et al.
4,897,481 A *  1/1990   Kershner et al. ............. 544/354

FOREIGN PATENT DOCUMENTS

EP        0 344 746 A2   6/1989
WO    WO/2009/055278     4/2009

* cited by examiner

*Primary Examiner* — Shawquia Young
(74) *Attorney, Agent, or Firm* — Michael R. Asam

(57) ABSTRACT

Cyhalofop is prepared by coupling 2-(4-hydroxyphenoxy) propionic acid and 3,4-difluorobenzonitrile with base in a polar aprotic solvent in the presence of a phase-transfer catalyst.

1 Claim, No Drawings

PROCESS FOR THE MANUFACTURE OF R-(+)-2-(4-(4-CYANO-2-FLUOROPHENOXY) PHENOXY)PROPIONIC ACID ESTERS

This application is a divisional application of U.S. patent application Ser. No. 12/251,005 filed on Oct. 14, 2008 and claims the benefit of U.S. Provisional Application Ser. No. 60/000,256 filed on Oct. 24, 2007. This invention relates to an improved process for the preparation of R-(+)-2-(4-(4-cyano-2-fluorophenoxy)phenoxy)propionic acid esters.

FIELD OF THE INVENTION

Background of the Invention

U.S. Pat. No. 4,897,481 discloses a process for minimizing the amount of racemization which occurs during the preparation of R-(+)-2-(4-(4-cyano-2-fluorophenoxy)phenoxy)propionate esters which comprises contacting an alkali metal salt of R-(+)-2-(4-hydroxyphenoxy)propionic acid with 3,4-difluorobenzo-nitrile (3,4-DFBN) in a polar aprotic solvent, particularly dimethyl sulfoxide, in the presence of an alkali metal carbonate and subsequently esterifying the resulting R-(+)-2-(4-(4-cyano-2-fluorophenoxy)phenoxy) propionic acid salt with an alkyl halide.

SUMMARY OF THE INVENTION

The present invention is directed to an improved process for the manufacture of R-(+)-2-(4-(4-cyano-2-fluorophenoxy)phenoxy)propionate esters of the formula

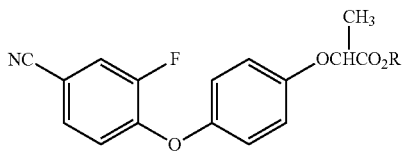

wherein R represents $C_1$-$C_8$ alkyl
which comprises:
a) forming the di (alkali metal salt) of R-(+)-2-(4-hydroxyphenoxy)-propionic acid by contacting R-(+)-2-(4-hydroxyphenoxy)propionic acid in a polar aprotic solvent, having a dipole moment of at least 2 or dielectric constant of at least 7 and having a normal boiling point of less than 175° C., with at least two equivalents of alkali metal carbonate;
b) forming R-(+)-2-(4-(4-cyano-2-fluorophenoxy)phenoxy)propionic acid alkali metal salt by coupling the di (alkali metal salt) of R-(+)-2-(4-hydroxy-phenoxy)propionic acid reaction mixture of step a) with 3,4-difluorobenzonitrile;
c) forming R-(+)-2-(4-(4-cyano-2-fluorophenoxy)phenoxy)propionic acid alkyl ester by alkylating the R-(+)-2-4-(4-cyano-2-fluorophenoxy)phenoxy)-propionic acid alkali metal salt reaction mixture of step b) with an alkyl halide;
d) removing and recovering the polar aprotic solvent either by adding previously prepared, dry, molten R-(+)-2-(4-(4-cyano-2-fluorophenoxy)phenoxy)-propionic acid alkyl ester to the reaction mixture of step c) and by distilling the polar aprotic solvent from the mixture, or by distilling the polar aprotic solvent from the mixture with agitation;
e) removing salt from the distillation bottoms of step d) by extracting the distillation bottoms with warm water and separating the aqueous brine from the organic layer; and
f) removing low boiling components such as water and unreacted 3,4-difluorobenzonitrile by distilling the organic layer from step e) under reduced pressure.

In a preferred embodiment of the invention, the reaction in step b) coupling the di (alkali metal salt) of R-(+)-2-(4-hydroxyphenoxy)propionic acid with 3,4-DFBN is performed in the presence of a phase-transfer catalyst.

DETAILED DESCRIPTION OF THE INVENTION

Throughout this document, all temperatures are given in degrees Celsius, and all percentages are weight percentages unless otherwise stated.

Unless specifically limited otherwise, the term "alkyl," as used herein, includes within its scope straight chain, branched chain and cyclic moieties.

Unless specifically limited otherwise, the term "halogen," as well as derivative terms such as "halo" and "halide" as used herein, refers to chlorine, bromine and iodine.

The term "alkali metal," as used herein, refers to the metals of Group IA of the periodic table. Preferred alkali metals are lithium, sodium and potassium.

The term "polar aprotic solvent", as used herein, refers specifically to those polar aprotic solvents having enough polarity to have dipole moment of at least 2 or dielectric constant of at least 7, and having enough volatility to have a normal boiling point of less than 175° C. Such polar aprotic solvents include, for example, acetonitrile, propionitrile, acetone, methyl ethyl ketone, methyl propyl ketone, methyl isobutyl ketone, 2-methoxyethyl acetate, dimethyl formamide, dimethyl acetamide, and the like, with acetonitrile being especially preferred.

The term "phase-transfer catalyst" is intended to mean a material which catalyzes a reaction by the transfer of reactants from one phase to another. Phase-transfer catalysts suitable for use in the present process include quaternary ammonium and phosphonium salts. Suitable quaternary ammonium and phos-phonium salts normally have an aggregate carbon content of at least 4 carbons to about 31 carbons, preferably from 4 carbons to about 16 carbons. The ammonium salts are currently preferred over the phosphonium salts due to cost and commercial availability. Suitable catalysts are tetramethyl ammonium bromide, tetraethyl ammonium chloride, methyl tributyl ammonium chloride, tetrabutyl ammonium hydrogen sulfate, benzyl tributyl ammonium chloride, benzyl trimethyl ammonium fluoride, bis-(tetramethyl ammonium) oxalate, dodecyltrimethylammonium bromide, tetrabutylammonium sulfate, methyl triphenyl phosphonium bromide, tributyl tetradecyl phosphonium chloride, tetradecyl phosphonium chloride, and the like.

R-(+)-2-(4-(4-cyano-2-fluorophenoxy)phenoxy)propionic acid butyl ester is an optically active rice herbicide known by the common name cyhalofop-butyl and sold under the tradenames Cleaner™ and Clincher™ (trademarks of Dow AgroSciences LLC).

In the first step of the process, R-(+)-2-(4-hydroxyphenoxy)propionic acid is neutralized with at least two equivalents of alkali metal carbonate. Typically, the alkali metal carbonate is slurried in the polar aprotic solvent. To this slurry is slowly added a heated solution of R-(+)-2-(4-hydroxyphenoxy)propionic acid in the polar aprotic solvent. The reaction is conducted at a temperature of about 50-80° C. and the addition rate and mixing intensity are controlled at a rate to keep the slurry well suspended and the evolution of $CO_2$ manageable.

In the second step of the process, about 0.9 to 1.1 equivalents of 3,4-DFBN are added to the reaction mixture of the first step at a temperature of about 50-80° C. The temperature is then raised to about 120-150° C. and held at that temperature until the reactants are converted to R-(+)-2-(4-(4-cyano-2-fluorophenoxy)phenoxy)propionic acid alkali metal salt. The 3,4-DFBN can be added either molten or as a solution in the polar aprotic solvent. It is often preferred to add a catalytic amount, typically from about 1 to about 5 weight percent based on the weight of 3,4-DFBN, of phase-transfer catalyst to this step. While this step can be conducted at the boiling point of the mixture, it is advantageous to conduct the reaction at elevated temperature, which results in pressure up to 100 pounds per square inch gauge (psig).

In the third step of the process, about 1.0 to about 1.2 equivalents of alkyl halide are added to the reaction mixture of the second step and the temperature is maintained at 80-110° C. and held at that temperature until R-(+)-2-(4-(4-cyano-2-fluorophenoxy)phenoxy)propionic acid alkali metal salt is converted into the corresponding alkyl ester. While the step can be conducted at the boiling point of the mixture, it is again advantageous to conduct the reaction at elevated temperature, which results in pressures up to 50 psig.

In the fourth step of the process, the polar aprotic solvent is removed from the reaction mixture by distillation and is recycled to subsequent batches. When the alkylation reaction of step 3 is completed, the reaction mixture is cooled and approximately 125 to 250 weight percent (based on the weight of 3,4-DFBN) of previously prepared molten R-(+)-2-(4-(4-cyano-2-fluorophenoxy)phenoxy)propionic acid alkyl ester is added as a flux to improve the suspension of the salts during the distillation. The mixture is distilled at reduced pressure until nearly all of the polar aprotic solvent has been removed overhead. Typically, the distillation is performed at a reduced pressure of from about 50-350 mm Hg and a bottoms temperature of about 90-130° C. The flux can be added after a portion of the polar aprotic solvent has been removed. Optionally, if agitation is sufficient to keep the salts suspended, no flux may be necessary.

In the fifth step of the process, the distillation bottoms from step 4 are cooled to about 50-70° C. and enough warm water is added to the post distillation slurry to make about a 30-35 percent alkali metal halide salt solution in the aqueous phase. The organic layer is decanted and washed again at about 50-70° C. with an additional similar amount of warm water and the layers are again separated.

In the last step of the process, the organic layer, consisting primarily of molten R-(+)-2-(4-(4-cyano-2-fluorophenoxy)phenoxy)propionic acid alkyl ester from the extraction of step 5, is dried by removing the residual water and any remaining 3,4-DFBN by distilling the organic layer under reduced pressure. Typically the organic layer is heated to a temperature of about 90-130° C. under a reduced pressure of about 10-100 mm Hg. The dried molten R-(+)-2-(4-(4-cyano-2-fluorophenoxy)phenoxy)propionic acid alkyl ester, which is suitable for sale as technical material, can be optionally filtered.

The following examples illustrate the invention.

Example 1

R-(+)-2-(4-(4-cyano-2-fluorophenoxy)phenoxy)propionic acid, n-butyl ester [cyhalofop-butyl]

To a 250-milliliter (mL) bottom-drain round bottom flask equipped with an overhead stirrer, cold water condenser, thermocouple, and a controlled infra-red heating lamp was added 42.1 grams (g) of R-(+)-2-(hydroxyphenoxy)-propionic acid [MAQ-Acid] and 71.6 g of acetonitrile. This mixture was stirred and heated to 75° C., by which time the MAQ-Acid had fully dissolved.

To a one-liter jacketed bottom-drain cylindrical flask equipped with an overhead stirrer, heating/cooling bath and cold water condenser was added 94.7 g of acetonitrile, 2.53 g of water and 74.7 g of powdered potassium carbonate (−325 mesh). This mixture was mixed and heated to 50° C.

The MAQ-Acid solution was then slowly dripped through a Teflon® tube directly from the solution flask into the $K_2CO_3$ slurry over about 2 hours. Upon completion of the addition, the temperature was raised to 75° C. and held for 1 hour.

This slurry was transferred to a 325-mL pressure vessel equipped with an overhead stirrer, thermocouple, controlled heating mantle, pressure relief and a pressure gauge. To the slurry was then added 33.1 g of 3,4-DFBN. The vessel was sealed; mixing was started and then the mixture was heated to 135° C. for 7 hours. The pressure reached 53 psig.

The vessel was cooled to 60° C., opened and 35.1 g of n-butyl bromide was added. The vessel was resealed, mixing was started and then the mixture was heated to 100° C. for 6 hours. The pressure reached 19 psig.

The vessel was cooled to 60° C. and the contents transferred to a 500-mL 3-neck bottom-drain round bottom flask equipped with an overhead stirrer, thermocouple, controlled heating mantle, 6-inch Vigreux column with a cold water condenser and 250-mL round bottom receiver, a secondary dry ice/acetone condenser with a 125-mL round bottom received, and a vacuum pump with variable vacuum control. To this slurry, 61.9 g of previously made cyhalofop-butyl was added (assay=96 percent). Mixing was started, vacuum was pulled to 200 mm Hg and heat was applied to remove acetonitrile. When the bottoms temperature reached 80° C., the vacuum was slowly reduced to 60 mm Hg. When the bottoms temperature reached 120° C., the distillation was stopped.

The slurry was cooled to 60° C. and 147 g of 50° C. water was added. The two-phase mixture was stirred for 15 minutes while maintaining a temperature of 50° C. Mixing was stopped and the resulting two phases allowed to settle for 15 minutes. The lower aqueous salt-containing phase was drained off To the upper phase was added 105 g of 50° C. water and the mixture again stirred for 15 minutes while maintaining a temperature of 50° C. Mixing was stopped and the resulting two-phase mixture was allowed to settle for 15 minutes. The lower cyhalofop-butyl phase was drained off and set aside, and the upper aqueous layer removed. The cyhalofop-butyl phase was returned to the flask. Vacuum was pulled to 60 mm Hg and heating applied to distill off entrained water. When the temperature reached 120° C., the distillation was stopped.

The mass of this final product was 141 g (assaying 96 percent cyhalofop-butyl), constituting an effective yield of 92 percent. The ratio of R(+)/S(−)cyhalofop-butyl isomers was 98.5/1.5.

Example 2

Use of Catalyst [Tetramethylammonium chloride (TMAC)] in Step b

Equipment was a 600-mL pressure vessel equipped with an overhead stirrer, thermocouple, heating mantle, pressure relief device, and pressure gauge. To the vessel was added 135 g of previously prepared R-(+)-2-(4-hydroxyphenoxy) propionic acid dipotassium salt, 152 g of acetonitrile, 39.8 g of 3,4-DFBN and 1.67 g of TMAC. The vessel was sealed and mixing started. The vessel was heated to 120° C. and held for 7 hours. The pressure reached ~30 psig.

The vessel was cooled to ~60° C., opened and 42.4 g of n-butyl bromide was added. The vessel was resealed and mixing was started the vessel was heated to 85° C. and held for 6 hours. The pressure reached ~8 psig.

The resulting post-reaction slurry (mass=371 g) was collected and analyzed. Product assay to R-(+) cyhalofop-butyl was 21.9 percent constituting a non-isolated yield of 94.9 percent (normalized to 97.0 percent). The ratio of R(+)/S(−)cyhalofop-butyl isomers was 99.7/0.3 in the post reaction mixture.

What is claimed is:

1. An improved process for the manufacture of R-(+)-2-(4-(4-cyano-2-fluorophenoxy)phenoxy)propionic acid alkali metal salt of formula

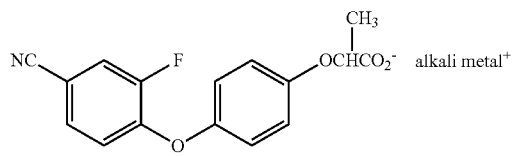

which comprises:

a) forming a di (alkali metal salt) of R-(+)-2-(4-hydroxyphenoxy)-propionic acid by contacting R-(+)-2-(4-hydroxyphenoxy)propionic acid in a polar aprotic solvent, having a dipole moment of at least 2 or dielectric constant of at least 7 and having a normal boiling point of less than 175° C., with at least two equivalents of alkali metal carbonate; and b) forming R-(+)-2-(4-(4-cyano-2-fluorophenoxy)-phenoxy)propionic acid alkali metal salt by coupling the di (alkali metal salt) of R-(+)-2-(4-hydroxy-phenoxy)propionic acid reaction mixture of step a) with 3,4-di-fluorobenzonitrile in the presence of a phase-transfer catalyst at a temperature from about 120° C. to about 150° C. in a sealed pressure vessel.

* * * * *